United States Patent
Xue et al.

(10) Patent No.: US 6,521,634 B2
(45) Date of Patent: Feb. 18, 2003

(54) USES OF DL-THP

(75) Inventors: Hong Xue, Clear Water Bay (HK); Sek Lun Law, Hong Kong (HK)

(73) Assignee: The Hong Kong University of Science & Technology, Hong Kong (HK)

( * ) Notice: Subject to any disclaimer, the term of this patent is extended or adjusted under 35 U.S.C. 154(b) by 0 days.

(21) Appl. No.: 09/819,367

(22) Filed: Mar. 28, 2001

(65) Prior Publication Data

US 2002/0143067 A1 Oct. 3, 2002

(51) Int. Cl.$^7$ ................................................ A61K 31/44
(52) U.S. Cl. ...................................................... 514/284
(58) Field of Search ......................................... 514/284

(56) References Cited

U.S. PATENT DOCUMENTS

| | | |
|---|---|---|
| 5,242,926 A | 9/1993 | Hsieh et al. |
| 5,308,619 A | 5/1994 | Schneider et al. |
| 5,547,956 A | 8/1996 | Qu et al. |

OTHER PUBLICATIONS

Tsung et al, Chemical Abstracts, vol. 61, abstract No. 48035, 1961.*
T'ang et al, Chemical Abstracts, vol. 59, abstract No. 71344, 1962.*
Chin et al, Chemical Abstracts, vol. 53, abstract No. 73843, 1957.*
Lai et al, Chemical Abstracts, vol. 130, abstract No. 263235, 1999.*
Hsieh et al, Chemical Abstracts, vol. 133, abstract No. 53621, 1999.*
Vinogradova et al, Chemical Abstracts, vol. 99, abstract No. 16385, 1983.*
Tang et al, Embase Online, abstract No. 1981079811, 1980.*

* cited by examiner

Primary Examiner—William R. A. Jarvis
(74) Attorney, Agent, or Firm—Dority & Manning, PA

(57) ABSTRACT

The present invention is concerned with new, previously unsuggested, therapeutic uses of dl-THP (dl-tetrahydropalmatine) including anxiety disorders, seizures, and status epilepticus.

7 Claims, 5 Drawing Sheets

USES OF DL-THP

FIELD OF THE INVENTION

The present invention concerns novel uses of dl-tetrahydropalmatine (dl-THP) and its related compounds, methods of treatment of patients in need of same, and methods of manufacture of medicaments for treatment of patients, and the use of dl-THP in same.

BACKGROUND OF THE INVENTION dl-THP (also known as Corydalis B, full name 5,8,18, 13a-tetrahydro-2,3,9,10-tetramethoxy-6H-dibenzo [a,q] quinolizine) is a well known compound which has in the past been shown to have a number of therapeutic effects. Reference herein to "therapy" in its various forms is to any treatment which is designed to cure, alleviate, remove or lessen the symptoms of, or prevent or reduce the possibility of contracting any disorder or malfunction of the human or animal body. U.S. Pat. No. 5,242,926 claims the treatment of hyperthyroidism using dl-THP. U.S. Pat. No. 5,308,619 claims the use of the active ingredient extracts of Corydalis and Eschscholtzia in treating states of agitation and nervous dysfinction. U.S. Pat. No. 5,547,956 discloses its use in methods for treating drug addicts' withdrawal symptoms. It is readily isolated from e.g. Corydalis yanhusuo W. T. Wang, a traditional Chinese medicine of which it is just one of the active ingredients, the plant being used for promoting blood circulation, reinforcing vital energy and alleviating pain. Corydalis yanhusuo can also palliate the stagnation of vital energy or blood stasis, which would otherwise result in headache, chest pain, hypochondriac pain, epigastric pain, abdominal pain, backache, arthralgia, dysmenofrhea or trauma dl-THP has been shown to deplete the levels of dopamine, noradrenaline and serotonin in the CNS (Liu G Q et al., Arch Int Pharmacodyn Ther July 1982;258(1):39–50; PMID 6182845), and to decrease both arterial pressure and heart rate through a serotonergic release process in the hypothalamus (Chueh F Y et al., Jpn J Pharmacol. October 1995;69(2): 177–80; PMID: 8569056). It also decreases motor activity. It is also known to be protective in rat heatstrokes (Chang C K et al., Neurosci Lett. May 28, 1999;267(2): 109–12; PMID: 10400224). Targets in the CNS for the two enantiomers (i.e. the d and l enantiomers) of dl-THP have been identified and therapeutic effects shown, including causing a sedative-tranquilizing effect and inhibiting voltage-dependent $Ca^{2+}$ channels (Vauquelin et al., Neurochemistry International, 1989 15(3):321–324).

dl-THP is widely available and is sold as being a herbal dietary supplement and as a sleeping pill.

A pharmacological study of dl-THP (Hsu B et al., Archives Internationales de Phannacodynamie 1962; CXXXIX: 318–327) on lab animals has shown it to have an analgesic effect. It has a sedative-tranquilizing action, decreases the toxicity of amphetamine, prevents abnormal activity cause by mescaline, causes an extinction of conditioned avoidance responses, and causes calming with marked sedation. Clinical trials in hospitals have shown in cases of dull visceral pain a marked analgesic effect for dl-THP, and that it is useful as a short acting hypnotic in patients with insomnia. Additional studies include those of Hsu B et al. (International Journal of Neuropharmacology 1964; 2:283–290).

The tranquilizing action of dl-THP has previously been considered to be related to the blocking of the DA receptor. However, previous studies have used the results of animal behavioral tests to determine receptor binding characteristics of dl-THP and its enantiomers rather than actual in vitro assays. Therefore prior studies have, as a result, been limited in their scope and the understanding of the action of dl-THP which they are able to provide.

BRIEF SUMMARY OF THE INVENTION

The present invention succeeds in identifying a previously unsuggested binding partner for dl-THP, namely the BDZ (benzodiazepine) binding site of the $GABA_A$ receptor (the gamma-aminobutyric acid) receptor. The dl-THP-GABA receptor interaction competitively inhibits other GABA receptor-BDZ interactions and provides novel observations of therapeutic effects achieved with dl-THP. This new understanding of the interactions of dl-THP provides the opportunity for previously unsuggested therapeutic uses of dl-THP.

According to the present invention there is provided a method of manufacture of a composition (e.g. a medicament) for the treatment of CNS disorders, including the treatment of anxiety and seizures, the composition comprising dl-THP (or one or more of its related compounds) and a physiologically acceptable carrier. In particular the composition may be an anxiolytic, or anticonvulsant. Part uses include the treatment of status epilepticus and cerebral palsy, seizure and generalized anxiety disorder (GAD), and as an anticonvulsant and anesthetic premedication. This contrasts with its previously reported effects such as its sedative-tranquilizing effect.

Also provided is a method of treatment of a CNS disorder as defined above in a patient, comprising administering to said patient a therapeutically effective quantity of dl-THP.

Also provided is the use of dl-THP in a method of manufacture of a medicament for the treatment of a CNS disorder as defined above.

DETAILED DESCRIPTION OF THE INVENTION

Figure 1:
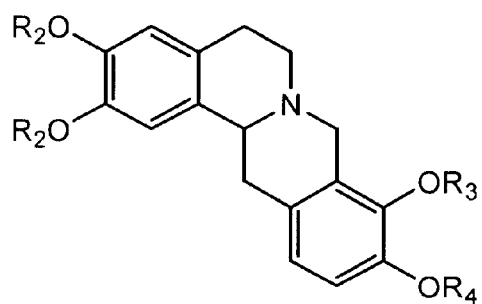
FIG. 1 shows the structure of the tetrahydroprotoberberine backbone.

GABA (gamma-aminobutyric acid) is regarded as one of the major inhibitory amino acid transmitters in the central nervous system (CNS) of the mammalian brain. GABA is synthesized from glutamic acid, the major excitatory neurotransmitter, by one of two forms of glutamic acid decarboxylase (GAD). About 30% of neurons in the brain, particularly small interneurons, are thought to be GABAergic (contain GAD), and most neurons will respond to GABA by reducing their firing rate. They are widely, although unequally, distributed through the mammalian brain. An enormous amount of effort has been devoted to implicating GABA in the etiology of anxiety, seizure disorder, sleep disorder and cognition (Tallman J F et al., "The GABA-ergic system: a locus of benzodiazepine action.", Annu Rev Neurosci. 1985;8:21–44; PMID: 2858999). GABA mediates many of its actions through GABA receptors localized both on cell bodies and on nerve endings. Postsynaptic responses to GABA are mediated through alterations in chloride conductance that generally lead to hyperpolarization of the cell. Recent research has found that the complex of proteins associated with postsynapfic GABA responses is a major site of action for a number of structurally unrelated compounds capable of modifying postsynaptic responses to GABA. Depending on the mode of interaction, these compounds are capable of producing a spectrum of effects, such as sedative, anxiolytic and anticonvulsant, or wakefulness, seizures and anxiety.

The $GABA_A$ receptor has a number of functional domains (Smith G B, Olsen R W, Trends Pharmacol Sci. 1995 May; 16(5):162–8; PMID: 7624971) and has, located in or near its chloride ion channel, a number of binding sites for benzodiazepines, barbiturates and picrotoxins, as well as sites for the anesthetic steroids. In particular, the gamma subunit appears to enable drugs like benzodiazepines to modify the GABA responses (Pritchett DB et al., Nature, April 13, 1989;338(6216):582–5; PMID: 2538761).

The class of benzodiazepines includes diazepam, trizolam and flunitrazepam. The principal behavioral effects of classical benzodiazepines in animals are four-fold: relief of anxiety, anticonvulsant effects, sedation and myorelaxation. These properties are shared by all full benzodiazepine agonists, regardless of the therapeutic indication for which they are prescribed. For instance, trizolam, prescribed as a hypnotic, is also a potent anxiolytic and anticonvulsant in animal tests, whereas diazepam, prescribed principally as an anxiolytic, is a powerful hypnotic in animals. It can be considered that all full agonists from other chemical series have equivalent behavioural effects. All these effects are blocked by benzodiazepine antagonists, indicating that they are indeed mediated by a direct interaction with the $GABA_A$ receptor.

Drugs that interact at the BDZ binding site of the $GABA_A$ receptor can possess a spectrum of pharmacological activities depending on their abilities to modify the actions of GABA. Those compounds that bind to the receptor and which possess activity similar to that of the BDZs are called agonists. Compounds that bind to the receptor and which possess activity opposite to that of the BDZs are called inverse agonists, and compounds which block both types of activity are termed antagonists.

When GABA binds to a $GABA_A$ receptor, the chloride ion flux through the channel is increased. This leads to membrane hyperpolarization that results in a reduction in the excitability potential of the neuron. Consequently, $GABA_A$ receptors are the molecular targets of a variety of pharmacologically and clinically important drugs, such as the anxiolytic, anticonvulsant, sedative-hypnotic BDZs, some anxiogenic, convulsant β-carbolines, and the convulsants bicuculline or picrotoxin. Furthermore, multiple recognition sites that exist within the three-dimensional structure of the various $GABA_A$ receptor subtypes possess the capacity to interact with a host of different ligands.

Thus the use of dl-THP in the present invention effects a response from the $GABA_A$ receptor. In particular, dl-THP can be used for the treatment of CNS disorders including the treatment of anxiety and seizures. Experiments undertaken by the inventors have shown dl-THP to be an agonist of the BDZ binding site of the $GABA_A$ receptor and to possess axiolytic, sedative and hypnotic properties. The sedative/hypnotic properties of dl-THP have been previously disclosed. The property of being an anxiolytic has not been previously suggested for dl-THP. Particular novel uses for dl-THP include the treatment of status epilepticus and cerebral palsy, seizure and generalized anxiety disorder (GAD, defined in e.g. A The $GABA_A$/Benzodiazepine receptor as a target for psychoactive drugs@, Springer, N.Y., 1995: 229–264; ISBN: 0412100916), and as an anticonvulsant and anesthetic premedication.

A number of advantages are shown by dl-THP when compared to other benzodiazepine drugs. In particular it has a low toxicity—its $LD_{50}$ in mice (oral administration), rats (oral administration) and mice (sub-cutaneous administration) are 1160 mg/kg, 930 mg/kg and 670 mg/kg, respectively. Additionally, it is readily obtainable from a wide range of traditional Chinese medicines such as *Corydalis yanhusuo* W. T. Wang, *Corydalis turtschaninovii* Bess. f. yanhusuo Y. H. Chou et C. C. Hsu, *Corydalis bulbosa* D. C., *Corydalis ambigua* Cham et Schleeht, *Corydalis nakaii* Ishidoya, *Corydalis aurea, Corydalis lutea, Corydalis ochroleuca, Corydalis cava, Corydalis solida, Stephania intermedia* Lo, *Stephania pierrei* Diels. and *Stephania viridiflaveus* using standard techniques well known in the art (see for example Matsuda H et al., "Inhibitory effects of methanolic extract from corydalis tuber against types I-IV allergic models.", Biol Pharm Bull. July 1995;18(7):963–7;

PMID: 7581251). It can also be synthesised using standard techniques (Narasimhan NS et al., "A novel synthesis of tetrahydropalmatine.", Chem Ind. May 10, 1969;19:621–2; PMID: 5781510).

Experiments

The experiments below show that dl-THP has an anxiolytic effect (i.e. that it is therapeutically effective in relieving or reducing anxiety, agitation and/or tension). They also show that it has a sedative effect, i.e. that it is therapeutically effective in the treatment of seizures. In particular its anxiolytic and sedative effects are useful in treating status epilepticus and cerebral palsy, seizure and generalized anxiety disorder (GAD).

Competitive Binding Study

Binding studies on dl-THP have previously been performed and have shown it to bind with the α-1 and α-2 adrenoceptors in rat cerebral cortex with a $K_i$ value of 4.70 μM and 4.97 μM respectively. Fluzitrazepam is a known BDZ and its binding affinity has been studied in, for example, Viola H et al. (Biochem Biophys Res Commun. Sep. 7, 1999;262(3):643–6; PMID: 10471378), Villar H O et al. (Mol Pharmacol. October 1989;36(4):589–600, PMID: 2554113) and Lelas S et al. (Behav Pharmacol. February 1999;10(1):39–50; PMID: 10780301).

Figure 7:
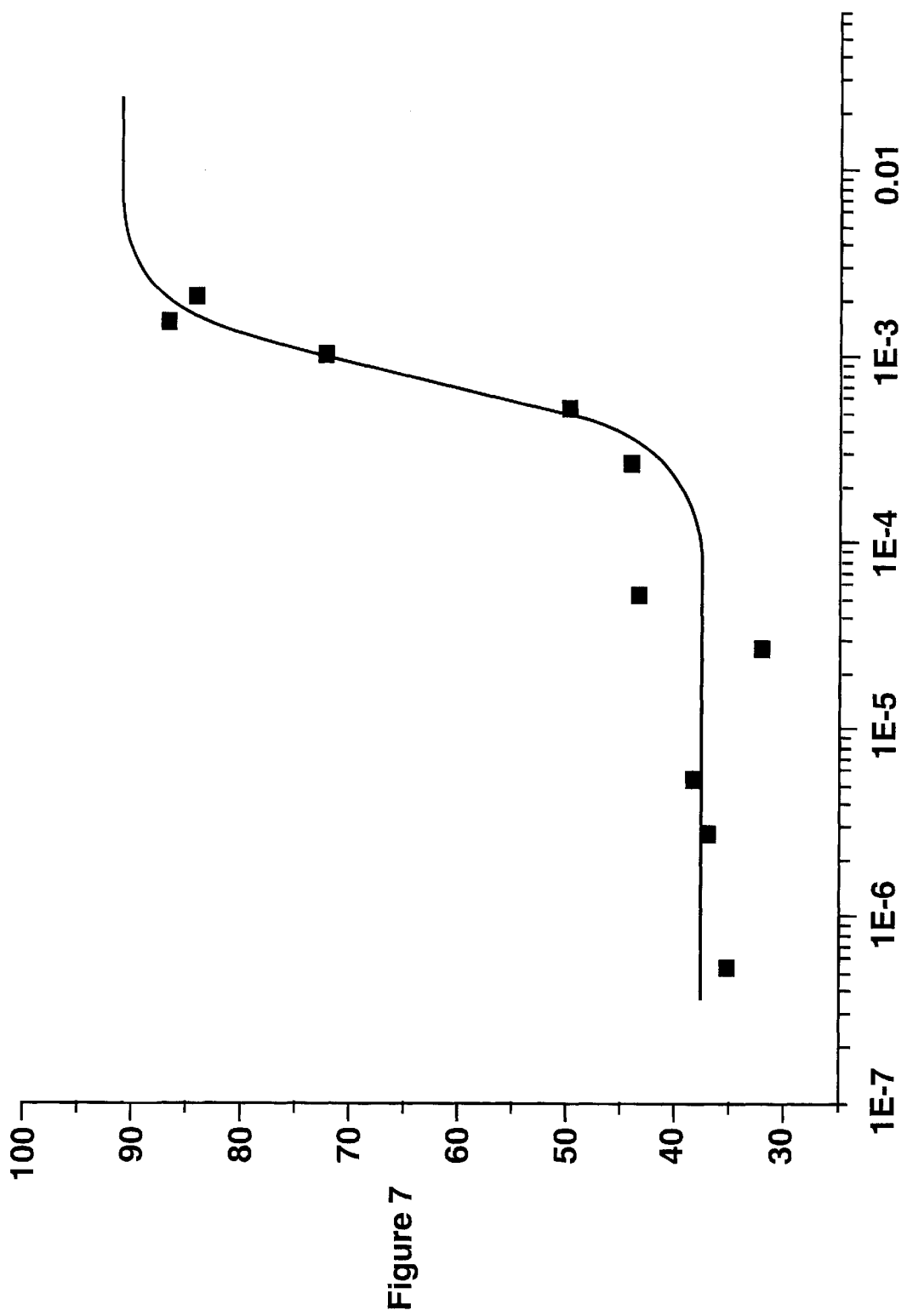
FIG. 7 shows the results of a standard competitive binding assay confirming that dl-THP inhibits the binding of [$^3$H]-flunitrazepam to the BDZ binding site of the $GABA_A$ receptor with an $IC_{50}$ value of 836.09 µM and a $K_i$ value of 517.58 µM.

Using a standard competitive binding assay (see FIG. 7), it was found that dl-THP inhibits the binding of [$^3$H]-flunitrazepam to the BDZ binding site of the $GABA_A$ receptor with an $IC_{50}$ value of 836.09 μM and a $K_i$ value of 517.58 μM.

Such competitive binding to the BDZ site of the $GABA_A$ receptor has not previously been suggested or shown for dl-THP.

Animals

ICR mice of either sex, weighing 14–17 g were used. Animals were housed in groups of four or five and were given food and water ad libitum and maintained on a 11 hour light: 13 hour dark cycle. All of the experimental groups had 12 animals per group.

Drugs dl-THP was dissolved in double distilled water and administered orally 1 hour before testing at concentrations as detailed below, with a total injection volume of 10 ml/kg. For the control group, double-distilled water was used as the vehicle.

Experimental Condition

All procedures were carried out in a quiet, air-conditioned laboratory between 08:00 and 13:00 at ambient temperature of 20–22° C. At the end of each session any boluses were removed and the box was thoroughly wiped with 70% ethanol.

Locomotor Activity Test

The ZIL-2 apparatus (Beijing Institute of Materia Medica) having dimensions of 60×60×12 cm was used to perform this test. It consists of four circular plastic boxes of 25 cm diameter, each having 6 equally distributed infrared photocells. The locomotor activity was counted automatically during a 5 minute test period. A decrease in the number of transitions reflects a decrease in locomotor activity.

Hole-board Test

The hole-board apparatus is a walled wood arena of 60×60×30 cm, with four equidistant 3 cm diameter holes spaced on the floor. The mice are placed on the center of the arena and the number of head-dips on the hole, the time spent head-dipping, the number of rearings and the time spent rearing are counted during a 5 minute test period (File SE et al., "The effects of triazolobenzodiazepines in two animal tests of anxiety and in the holeboard.", Br J Pharmacol. November 1985;86(3):729–35; PMID: 2866006). After each trial, the floor of the apparatus was wiped and dried thoroughly with tissue to remove traces of the previous path. A decrease of the four parameters as compared with the control group reveals a sedative behavior.

Elevatedplus-maze Test

The elevated plus-maze is made of wood as a horizontal cross consisting of two open arms (25×5 cm) and two opposite arms (25×5 cm) enclosed by 20 cm high walls. The arms extend from a central platform having dimensions of 5×5 cm. The plus-maze is elevated to a height of 40 cm from the floor. The maze is put inside a box with dimensions of 30×30×50 cm. After the hole-board test, the mice are immediately placed on the central platform of the maze facing a closed arm. The number of arm entries and the time spent into the open and closed arm are counted for 5 minutes (Pellow S et al., "Anxiolytic and anxiogenic drug effects on exploratory activity in an elevated plus-maze: a novel test of anxiety in the rat.", Pharmacol Biochem Behav. March 1986;24(3):525–9; PMID: 2871560). Arm entry was defined as all four feet in the arm. The total number of arm entries provided a measure of general activity. A selective increase in the parameters corresponding to open arms reveals an anxiolytic effect.

Horizontal-wire Test

The mice are lifted by the tail and allowed to grasp a horizontally strung wire (1 mm diameter, 15 cm long and placed 20 cm above the table) with their forepaws and released (Bonetti E P et al., Psychophannacology (Berl). 1982;78(1):8–18; PMID: 6292984). The number of mice out of ten that did not grasp the wire with their forepaws or actively grasped the wire with at least one hind paw within 3 seconds was determined.

Statistics

The results from the locomotor activity test and the elevated plus-maze test are expressed as mean±standard error of mean (SEM). All data were submitted to analysis of variance (ANOVA). Post hoc comparisons between individual treatments and controls of the locomotor activity test, the hole-board test and the elevated plus-maze test were made using Dunnett's t-test. The level of significance was considered to be $p<0.05$.

Results

FIG. 1 shows the typical phannacological profile of decreasing locomotor activity by the dl-THP. The dosages of 1 mg/kg and 10 mg/kg dl-THP both reduced by 33% ($F_{1,22}=20.29$, $p<0.0005$ and $F_{1,22}=25.09$, $p<0.0001$, respectively) locomotor activity, and the dosage of 30 mg/kg reduced by 36% ($F_{1,22}=22.62$, $p<0.00001$) locomotor activity.

When tested in the elevated plus-maze (FIG. 2), dl-THP did not significantly alter the total number of arm entries made by mice in the three different dosages ($F_{3,44}=0.56$). In a dose-dependent manner, dl-THP (1, 10 and 30 mg/kg, orally) significantly elevated both the percentage of open arm entries ($F_{3,44}=17.70$, $p<0.0000005$) and of time spent on the open arms ($F_{3,44}=23.32$, $p<0.000000005$); Dunnett's test showed that at 1 mg/kg dl-THP significantly differed from controls. These effects confirm that dl-THP has an anxiolytic effect (i.e. that it is an effective anxiolytic).

In the hole-board test (FIG. 3), dl-THP had significant effects on the number of head-dips and time spent head-dipping ($F_{3,44}=4.95$, $p<0.01$; $F_{3,44}=3.33$, $p<0.05$, respectively). Analysis showed that at the highest dose (30 mg/kg) dl-THP significantly reduced the number of head-dips and the time spent head-dipping ($F_{1,22}=16.83$, $p<0.0005$; $F_{1,22}=11.72$, $p<0.005$, respectively). Dunnett's test showed that at 10 mg/kg dl-THP significantly reduced the number of head-dips. These effects show that high doses of dl-THP have a sedative effect, i.e. that it is of use in the treatment of seizures. In the horizontal-wire test, dl-THP up to 30 mg/kg orally was without effect, which showed that dl-THP had no muscle-relaxant effect at this or a lower dose.

CONCLUSIONS

Figure 2:
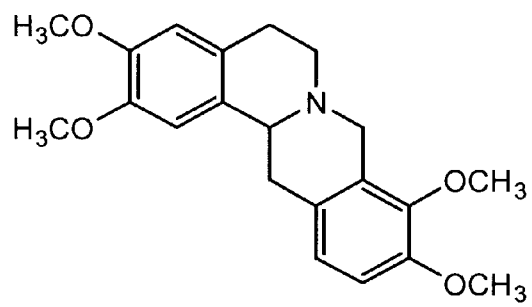
FIG. 2 shows the structure of dl-THP.
Figure 3A:
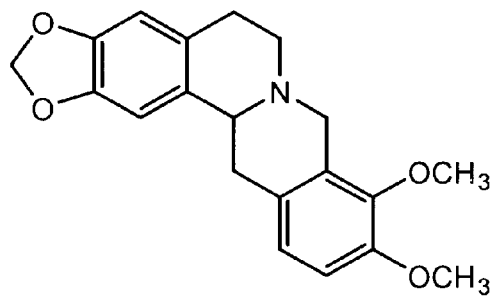
FIGS. 3a–c show the structure of, respectively, dl-tetrahydroberberine, l-scoulerine and α-allocryptopine.
Figure 3B:
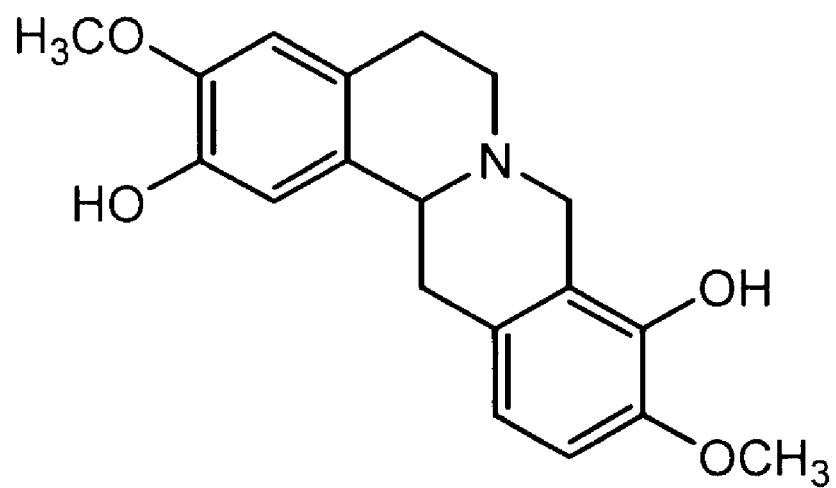
Figure 3C:
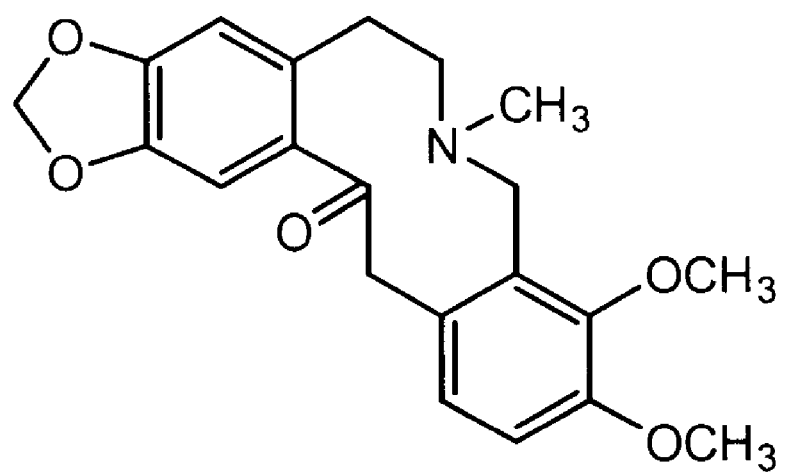
Figure 4:
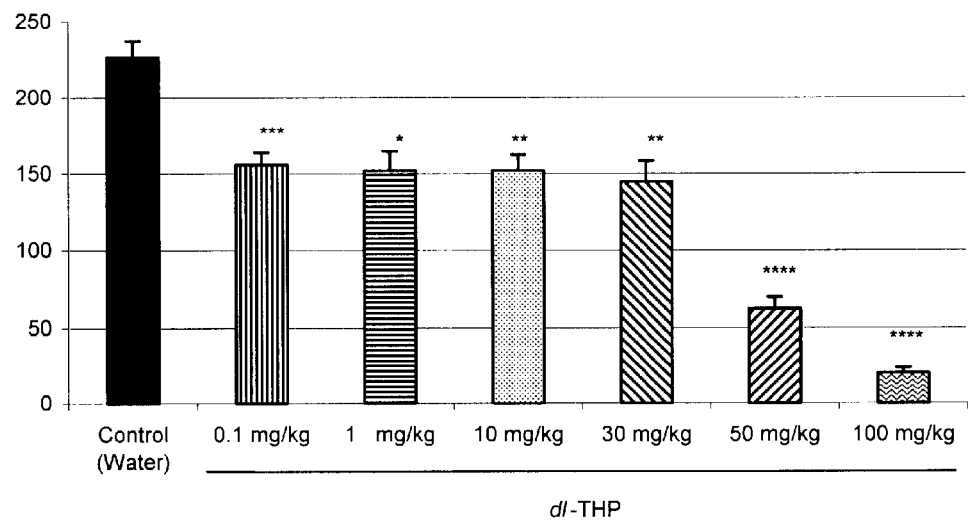
FIG. 4 shows the performance of mice given a 5 minute locomotor activity test. Y-axis shows number of transitions. Columns on the left axis are (left-right): control—1 hour after oral administration of a pharmaceutical carrier vehicle (water, control); 0.1 mg/kg, 1 mg/kg, 10 mg/kg, 30 mg/kg 50 mg/kg and 100 mg/kg of dl-THP. Results are expressed as the mean±SEM of the number of transitions. * $p<0.0005$, significantly different from controls (AVONA with Dunnett's t-test).  $p<0.0001$, significantly different from controls (AVONA with Dunnett's t-test). * $p<0.00005$, significantly different from controls (AVONA with Dunnett's t-test ). **** $p=0$, significantly different from controls (AVONA with Dunnett's t-test)
Figure 5:
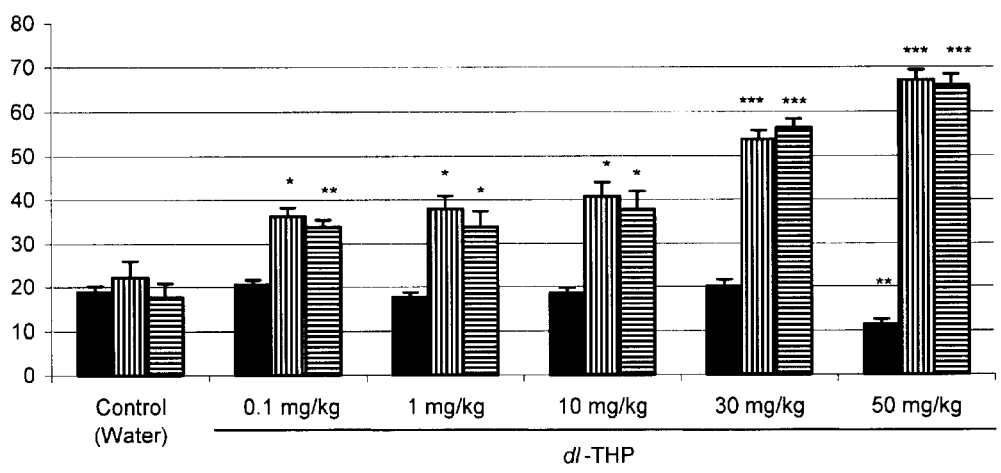
FIG. 5 shows the performance of mice given a 5 minute test in the elevated plus-maze. Y-axis shows (solid bars) the mean±SEM of the number of total entries, (vertically hatched bars) percentage of open arm entries, and (horizontally hatched bars) percentage of time (in seconds) spent in the open arm. X-axis shows results for (left-right) control—1 hour after oral administration of a pharmaceutical carrier vehicle (water); 1 mg/kg, 10 mg/kg, 30 mg/kg and 50 mg/kg of dl-THP. * $p<0.005$, significantly different from controls (AVONA with Dunnett's t-test).  $p<0.0000005$, significantly different from controls (AVONA with Dunnett's t-test). * p<0.000000001, significantly different from controls (AVONA with Dunnett's t-test)
Figure 6:
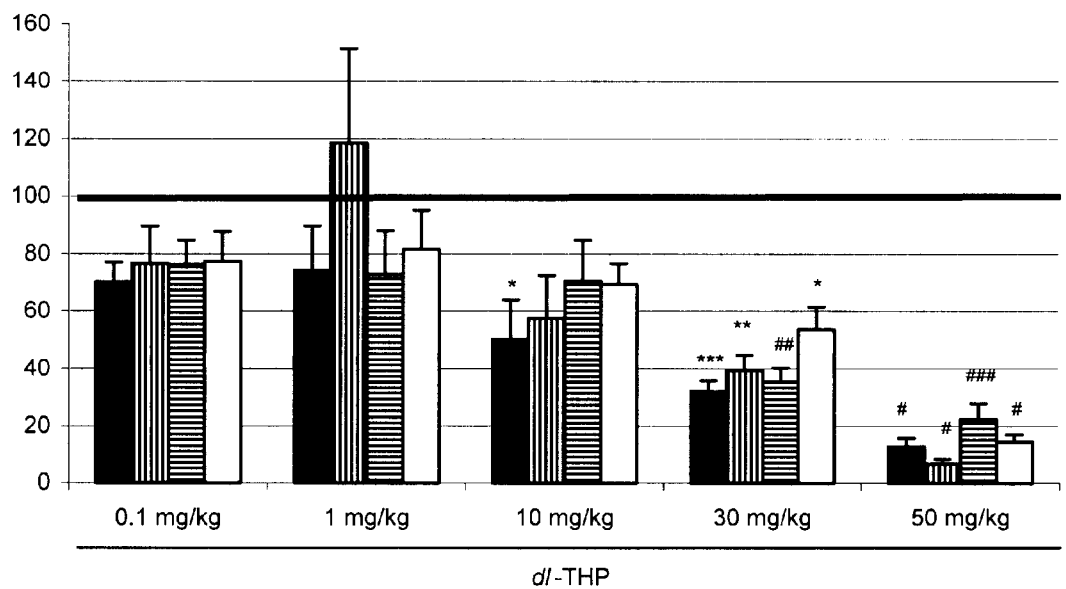
FIG. 6 shows performance of mice given a 5 minute test in the hole-board. Y-axis shows (solid bars) the percentage±SEM compared to control values of the number of head-dips, (vertically hatched bars) time spent head-dipping, (horizontally hatched bars) the number of rearings, and (open bars) the time spent on rearings. Control values were taken 1 hour after oral administration of a pharmaceutical carrier vehicle (water). X-axis shows results for (left-right) 0.1 mg/kg, 1 mg/kg, 10 mg/kg, 30 mg/kg and 50 mg/kg of dl-THP. * p<0.005 significantly different from controls (AVONA with Dunnett's t-test).  p<0.005 significantly different from controls (AVONA with Dunnett's t-test). * p<0.0005 significantly different from controls (AVONA with Dunnett's t-test). # p<0.00005 significantly different from controls (AVONA with Dunnett's t-test). ## p<0.00001 significantly different from controls (AVONA with Dunnett's t-test). ### p<0.000001 significantly different from controls (AVONA with Dunnett's t-test).

The main finding of the experiments is that dl-THP has anxiolytic effects in the elevated plus-maze test and sedative effects in the hole-board test without inducing muscle relaxation (FIGS. 2 and 3).

Therapeutically effective anxiolytic and sedative compositions used for treating anxiety and seizures, particularly status and cerebral palsy, seizure and generalized anxiety disorder, and for use as an anticonvulsant and anesthetic premedication consist dl-THP formulated with a physiologically acceptable carrier, diluent or excipient (Remington's Pharmaceutical Sciences and US Pharmacopoeia, 1984, Mack Publishing Company, Easton, Pa., USA; United States Pharmacopoeia, ISBN: 1889788031). Reference herein to physiologically acceptable carriers is also reference to physiologically acceptable diluents and excipients as appropriate.

Exact dosages for a given therapeutic effect are dependent upon a number of factors, particularly the age, weight and sex of the patient to whom the composition is to be administered. Optimal dosages for a given therapeutic effect are determined using simple dose-response assays.

A typical composition for oral administration consists of 2800 mg of dl-THP and a physiologically acceptable carrier.

The experiments above show administration of therapeutically effective quantities of dl-THP to mice. It can readily be administered to other mammals to achieve the same therapeutic effects, and particularly to humans, canines and felines as well as other domesticated animals and e.g. bovines and equines.

The contents of each of the references discussed herein, including the references cited therein, are herein incorporated by reference in their entirety.

Where "PMID:" reference numbers are given for publications, these are the PubMed identification numbers allocated to them by the US National Library of Medicine, from which full bibliographic information and abstract for the publication is available at www.ncbi.nlm.nih.gov. This can also provide direct access to electronic copies of the publications, particularly in the case of e.g. PNAS and JBC publications.

What is claimed is:

1. A method of treating a central nervous system disorder in a patient in need thereof comprising administering to said patient a therapeutically effective amount of dl-THP, wherein said central nervous system disorder is selected from the group consisting of anxiety disorders, seizures, and status epilepticus.

2. A method of preventing convulsions in a patient in need thereof comprising administering a therapeutic amount of dl-THP.

3. A method of anesthetizing a patient in need thereof comprising administering to said patient a therapeutic amount of dl-THP.

4. A method of treating a central nervous system disorder associated with the $GABA_A$ receptor benzodiazepine site in a patient in need thereof comprising:

supplying an effective amount of dl-THP to a patient; and,
binding the dl-THP to the $GABA_A$ receptor, thereby modifying a GABA regulatory process, said process including anxiety disorder, seizures, and status epilepticus within a patient.

5. A method according to claim 4 wherein said method of treating central nervous system disorders further includes the step of maintaining a muscular relaxation state at a pre-treatment level.

6. The method according to claim 1 wherein said anxiety disorder further includes generalized anxiety disorder.

7. The method according to claim 4 wherein said anxiety disorder further includes generalized anxiety disorder.

* * * * *